United States Patent [19]
Biedermann et al.

[11] Patent Number: 5,681,319
[45] Date of Patent: Oct. 28, 1997

[54] LOCKING TOOL

[76] Inventors: Lutz Biedermann, Am Schäfersteig 8, 78048 VS-Villingen; Jürgen Harms, Vogesenstrasse 60, 76337 Waldbronn, both of Germany

[21] Appl. No.: 607,681

[22] Filed: Feb. 26, 1996

[30] Foreign Application Priority Data

Mar. 1, 1995 [DE] Germany .......................... 195 07 141.7

[51] Int. Cl.$^6$ .................................................. A61B 17/88
[52] U.S. Cl. ................... 606/104; 606/73; 606/61
[58] Field of Search ................... 606/60, 61, 72, 606/73, 104

[56] References Cited

U.S. PATENT DOCUMENTS 5,304,179  4/1994  Wagner ................................. 606/61

FOREIGN PATENT DOCUMENTS

9215561 U  2/1993  Germany .
43 07 576  4/1994  Germany .

*Primary Examiner*—Michael Buiz
*Assistant Examiner*—David O. Reip
*Attorney, Agent, or Firm*—George W. Neuner

[57] ABSTRACT

A locking tool is described for connecting a bone screw with a rod having a predetermined diameter. The bone screw includes a screw member having a threaded portion and a head with spherical segment-shaped portion, and a cylindrical seat part for receiving the head and the rod. The seat part has two ends with a first bore at one end through which the threaded portion passes. An inner hollow spherical portion corresponding to the head is adjacent to the first bore. A second bore opens toward the opposite end for inserting the threaded portion and the head. A substantially U-shaped portion is provided with two free leg members for receiving the rod, the leg members having an internal screw thread. The locking tool has a handle part with a casing having two ends. An external screw thread on the first end engages the internal screw thread of the bone screw leg members. A pressure piece acts upon the head when screwing the external screw thread into the bone screw. A bolt for supporting the pressure piece on the first end provides rotation relative to the first end about a central axis of the handle part. The pressure piece has at least one projection for acting upon the head. The projection is spaced from the central axis by a distance which is at least equal to half of the predetermined diameter of the rod.

12 Claims, 2 Drawing Sheets

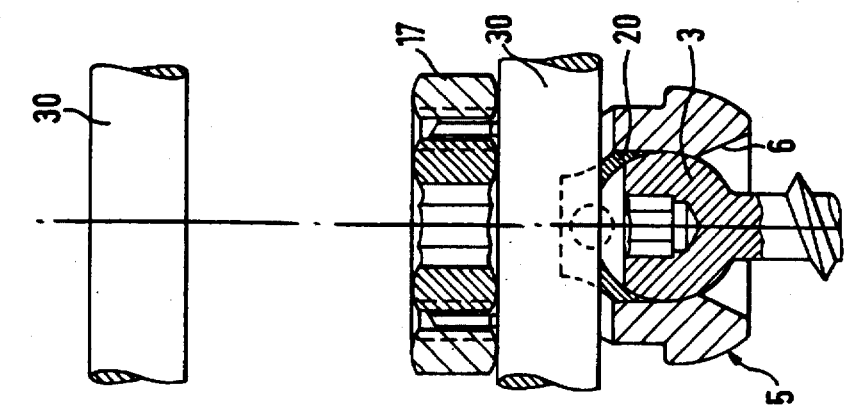
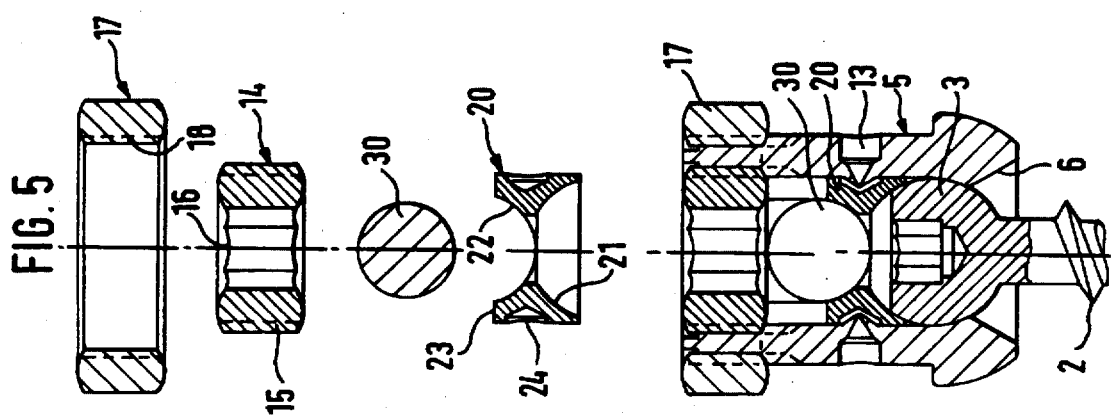
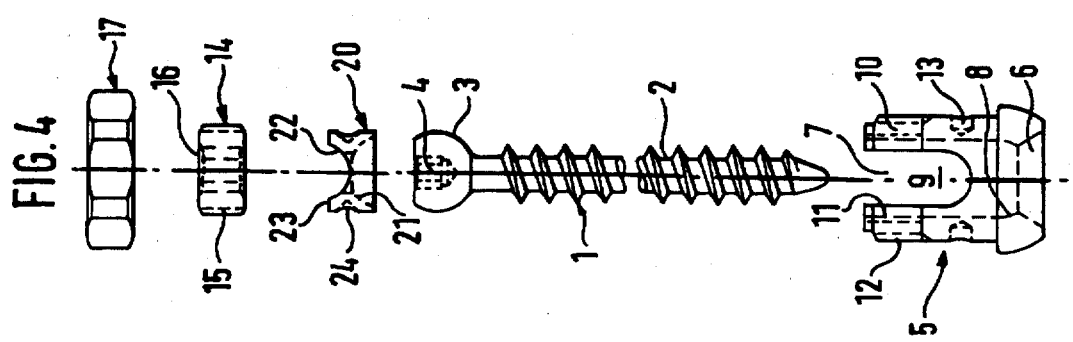
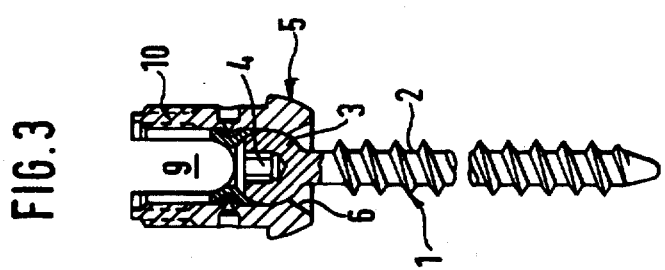

LOCKING TOOL

BACKGROUND OF THE INVENTION

The invention relates to a locking tool for locking movement of a seat part relative to a head of a polyaxial bone screw.

A polyaxial bone screw having a seat part and a head is disclosed in German patent 43 07 576. The bone screw has a threaded member and the position of this threaded member relative to the seat part is fixed by a pressure disk acting upon the head of the screw member by urging the pressure disk against the head of the screw member via the inserted rod and a rod locking screw. This creates the problem that when loosening the rod locking screw, the lock of the head of the screw, member with respect to the seat part is simultaneously released. Thus, each time the position of the seat part on the rod connecting the vertebrae is readjusted by means of a tool the seat part is also moved with respect to the head of the screw member, which is disadvantageous.

OBJECTS OF THE INVENTION

It is an object of the invention to provide a locking tool which avoids the above mentioned drawbacks. It is a further object to provide a locking tool which allows a relative displacement of the seat part and the rod for adjustment purposes but retains the lock between the seat part and the screw member.

SUMMARY OF THE INVENTION

In order to achieve the above mentioned objects the invention provides a locking tool for a bone screw for connection with a rod having a predetermined diameter, the bone screw comprising a screw member having a threaded portion and a head with a spherical segment-shaped portion, a cylindrical seat part for receiving the head and the rod, the seat part having a first end and an opposite second end, a first bore at the first end for passing the threaded portion therethrough, an inner hollow spherical portion adjacent to the bore for fitting the head, a second bore opening towards the second end for inserting the threaded portion and the head, and a substantially U-shaped portion comprising two free leg members for receiving the rod therebetween, the leg members having an internal screw thread, the locking tool comprising a handle part having a casing with a first end and a second end, a face at the first end and an external screw thread at a portion of the casing adjacent to the first end for engagement with the internal screw thread of the bone screw, a pressure piece for acting upon the head when screwing the external thread into the internal thread of the bone screw, means for supporting the pressure piece at the face of the handle part so as to be rotatable around the central longitudinal axis of the externally threaded portion of the handle part, the pressure piece having a projection for engagement with the head, the projection being spaced from the central logitudinal axis by a distance which is at least equal to half of the predetermined diameter of the rod.

BRIEF DESCRIPTION OF THE DRAWINGS

Further advantages, features and objects of the invention will be apparent from the following description of an exemplary embodiment with reference to the drawings, wherein

FIG. 3 is a sectional view of the bone screw of FIG. 1;

FIG. 4 shows the components of the bone screw of FIG. 3 with locking members in exploded representation;

FIG. 5 is a sectional view of the bone screw of FIG. 4 with inserted rod on an enlarged scale; and FIG. 6 is an enlarged sectional representation of the bone screw of FIG. 4 seen in a direction perpendicular to that of FIG. 5.

DESCRIPTION OF A PREFERRED EMBODIMENT

Figure 1:
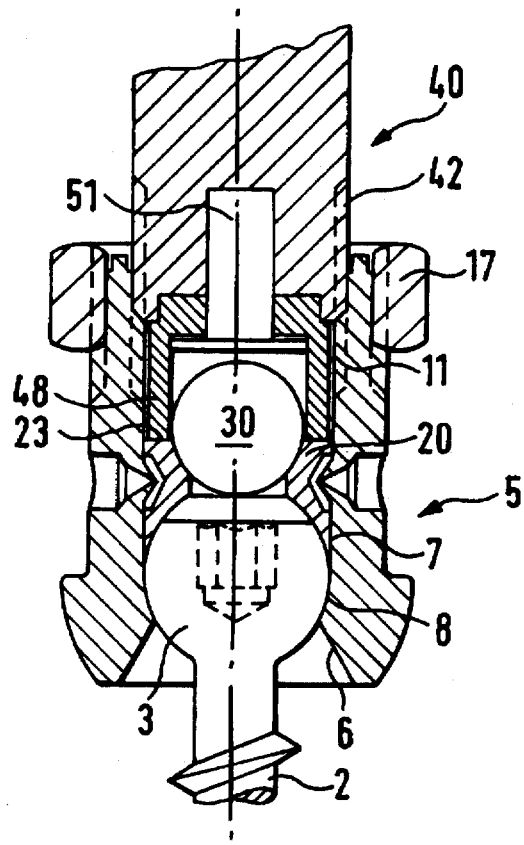
FIG. 1 is a sectional view of a lower part of the locking tool screwed into the seat part of a bone screw with inserted rod.

As best shown in FIGS. 3 and 4 the bone screw comprises the proper screw member 1 with a threaded shaft 2 and a head 3. The head 3 is formed as a spherical segment in a region adjacent to the threaded shaft 2. The head 3 has a recess 4 for engagement with a hexagon socket screw key at its face opposite to the threaded shaft 2 and a coaxially therewith.

The bone screw further comprises a cylindrical seat part 5 for receiving the head 3 of the screw member 1. At its one end the seat part has an axially symmetric first bore 6 with a diameter which is larger than that of the threaded shaft 2 and smaller than that of the head 3. The seat part 5 further comprises a coaxial second bore 7 which is open at the end opposite to the first bore 6 and has a diameter so that the screw member can be inserted from the open end to pass the threaded shaft through the first bore until the head 3 abuts the base of the second bore. A small coaxial portion 8 is formed immediately adjacent to the first bore 6 with a spherical shape towards the open end between the first and second bore. The radius of the spherical portion 8 corresponds substantially to the radius of the spherical segment-shaped portion of the head 3. The seat part 5 further comprises a U-shaped recess 9 which is symmetric with respect to the center axis of the threaded shaft 2 and has a base directed to the first bore 6 and two lateral legs 10 extending from the base to the open end opposite to the first bore 6. The channel formed by the U-shaped recess 9 is of a size to just fit a rod 30 placed therein for connecting the vertebrae. A bore having an internal screw thread 11 is formed in the interior of the channel defined by the U-shaped recess 9 coaxial with the center axis of the threaded shaft 2. The seat part 5 further has an external screw thread 12 formed at the outer surface of the legs 10 and adjacent to the free end thereof.

A pressure member 20 acting upon the head 3 of the screw member is provided for locking the position of the head 3 within the seat part 5. The pressure member 20 has an outer diameter selected so as to allow a sliding motion of the pressure member within the second bore 7 of the seat part 5, i.e. it can be displaced therein towards the head 3. At its side facing the head 3 the pressure member has a spherical countersink 21 with a radius which substantially corresponds to the radius of the spherical segment shaped portion of the head 3. At its side opposite to the head 3 the surface of a pressure member has a recess 22 formed as a cylinder portion extending perpendicular to the screw axis. The radius of curvature of the partial cylindrical recess 22 corresponds to the radius of curvature of the base of the U-shaped recess 9. The lateral walls of the pressure member 20 defined by the partial cylindrical recess 22 each have a plane surface 23 at their upper side opposite to the screw head 3. The lateral walls of the pressure member 20 defined by the partial cylindrical recess further have a blind bore 24 provided at the circumferential surface facing the inner wall of the seat part 5. The blind bores 24 are aligned with corresponding pocket bores 13 within the outer wall of the seat part 5 if the pressure member 20 rests on the head 3. In an assembled state (FIG. 5) the rod 30 is pressed onto the pressure member 20 by means of the nut 17. The pressure is transmitted onto the head 3 and locks a movement of the head 3 relative to the seat part 5.

Figure 2:
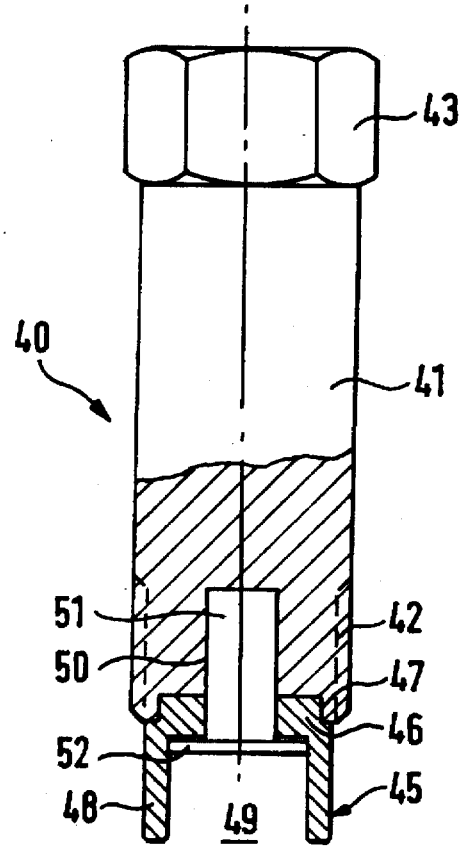
FIG. 2 is a side view of a locking tool in partially sectional representation.

A locking tool 40 shown in particular in FIGS. 1 and 2 is provided for locking the position of the pressure member 20 on the screw head 3 and for simultaneous release of the rod 30 to allow adjustment thereof. The locking tool 40 comprises a cylindrical handle part 41 and an adjacent fork-shaped pressure piece or projection piece 45. An external screw thread 42 for engaging the internal screw thread 11 of the legs 10 of the seat part 5 is provided at the cylindrical handle part 41 adjacent to the fork-shaped projection piece. The other end of the cylindrical handle part 41 is formed with a portion 43 having hexagon surfaces for engagement with a wrench.

The fork-shaped projection piece 45 has a cylindrical first portion 46 received within a coaxial cylindrical recess 47 provided at the face of the handle part 41. The first portion 46 has an outer diameter so that it can easily rotate within the recess 47. The fork-shaped projection piece further has a second portion adjacent to the first portion 46 on its side opposite to the handle part 41. The second portion comprises two free legs 48 formed as a fork. The legs 48 are each formed as a cylinder segment with a central longitudinal axis extending parallel to the central longitiudinal axis of the handle part 41. The distance between the respective outer surfaces of the legs 48 is smaller than the inner diameter of the second bore 7. The spacing between the plane inner surfaces of the legs 48 is larger than the diameter of the rod 30 to be inserted therebetween to allow the rod to move up and down in axial direction between the legs 48. The length of the legs 48 is selected to leave a gap for displacing the rod between the side of the rod 30 opposite to the screw head and the lower side of the first portion 46 of the fork-shaped projection piece 45 facing the rod with the rod 30 being inserted and the locking tool 40 being screwed into the seat part 5 until the legs 48 abut the surfaces 23 of the pressure member.

The fork-shaped projection piece 45 is rotatably connected with the handle part 41. This is realized by means of a bolt 51 passing through the cylindrical portion 46 and fixed, for example by a pressure fit, within a coaxial bore 50 at the part 41. The bolt 51 carries a disc 52 at its end opposite to the part 41. The diameter of the disc 52 is smaller than the spacing between the legs 48 by an amount which is just sufficient to allow a smooth rotation of the disc 52 between the legs 48. The length of the bolt is selected to create a small gap between the disc 52 and the cylindrical first portion 46. Thus, the disc 52 together with the part 41 is rotatable with respect to the fork-shaped projection piece 45. The cylindrical part 41 can therefore be screwed into the seat part 5 even with a rod placed therein.

As best shown in FIGS. 4 to 6 a member embracing the outside of the two U-shaped lateral legs 10 is provided in the form of a swivel nut 17 having an internal screw thread 18 cooperating with the external screw thread 12 of the two lateral legs 10 of the seat part 5. A locking member 14 formed as a threaded screw provides the final lock of the anchoring screw 1 with respect to the rod 30. The locking member 14 comprises an external screw thread 15 cooperating with the internal screw thread 11 for screwing the locking member into the U-shaped recess 9 of the seat part 5. Further, the locking member 14 comprises a hexagon recess 16 for engagement with a hexagon socket screw key.

All components of the described locking tool and screw member are made of a physically friendly material, in particular of titanium.

In operation the threaded shaft 2 is first inserted into the seat part from above through the second bore 7 of the seat part until the screw head of the screw member abuts the hollow spherical portion 8 of the seat part 5. The screw can then be anchored within the bone. For adjusting the position of the screw or of the threaded shaft 2, respectively, relative to the seat part 5 the pressure member 20 is pushed into the seat part 5 from its open side between the legs 10 until its spherical countersink 21 abuts the screw head 2. In the course of this the pressure member 20 is oriented with respect to the axis of the cylindrical bore 7 so that the axis of the partial cylindrical recess 22 of the pressure member 20 is exactly positioned in the plane of symmetry of the U-shaped channel 9 of the seat part 5. This position is obtained by slight crimping using the crimp bores 13 without impeding a sufficient movement of the pressure member in axial direction of the second bore 7. Thereafter, the rod 30 is inserted into the seat part 5 through the U-shaped recess 9.

As best shown in FIG. 1 the locking tool 40 is then screwed into the seat part 5 with the external screw thread 42 of the locking tool engaging the internal screw thread 11 of the legs 10 until the forks 48 of the fork-shaped projection piece 45 firmly abut the plane surfaces 23 of the pressure member 20 in a desired relative position of threaded shaft 2 of the screw member and seat part 5, and urge the pressure member onto the head 3 to block any relative movement. Since the forks 48 merely touch the sides of the rod 30 without however exerting a clamping force onto the rod the seat part 5 can be easily displaced with respect to the rod 3 for adjustment purposes.

As long as the locking tool 40 is screwed into the seat part 5 and locks the relative position of the seat part and the screw member 1 the swivel nut 17 is only loosely screwed onto the seat part 5 so that the rod 30 is not clamped thereby. After adjusting the desired position of the seat part 5 on the rod the rod 30 is firmly clamped by tightening the swivel nut 17.

In operation a respective bone screw is arranged in each segment of the spinal column, whereby a precise adjustment is made segment after segment for adjusting the engagement position of the individual bone screws at the rod relative to the longitudinal axis of the rod. As soon as the final position of a bone screw relative to the rod has been determined the rod 30 is locked in the seat part by means of the swivel nut 17 and at the same time the swivel nut 17 also presses the rod 30 into the partial cylindrical recess 22 of the pressure member 20 to also lock the screw head 3. Subsequently the locking tool is screwed out. Thereupon the locking member 14 is screwed in between the legs 10 in direction towards the rod for locking the same. The locking member secures the nut 17.

Although the invention has been described with reference to a specific example embodiment it is to be understood that it is intended to cover all modifications and equivalences within the scope and spirit of the amended claims.

What is claimed is:

1. A locking tool for a bone screw for connection with a rod having a predetermined diameter, said bone screw comprising a screw member having a threaded portion and a head with spherical segment-shaped portion, and a cylindrical seat part for receiving said head and said rod, said seat part having one end and an opposite end, a first bore at said one end for passing said threaded portion therethrough, an inner hollow spherical portion adjacent to said first bore for fitting said head, a second bore opening towards said opposite end for inserting said threaded portion and said head, and a substantially U-shaped portion comprising two free leg members for receiving said rod there-between, said leg members having an internal screw thread, said locking tool comprising:

a handle part having a casing with a first end and a second end;

an external screw thread on said first end for engagement with said internal screw thread of said bone screw;

a pressure piece for acting upon said head when screwing said external screw thread into said internal screw thread; and means for supporting said pressure piece on said first end so as to be rotatable relative to said first end about a central longitudinal axis of said handle part, said pressure piece having at least one projection for acting upon said head, said projection being spaced from said central longitudinal axis by a distance which is at least equal to half of said predetermined diameter of said rod.

2. The locking tool of claim 1, wherein said pressure piece is fork-shaped and comprises two spaced projections.

3. The locking tool of claim 2, wherein said pressure piece is supported on said first end of said handle part by means of a central bolt.

4. The locking tool of claim 2, wherein said two projections of said fork-shaped pressure piece are spaced from each other by a distance which is greater than said predetermined diameter of said rod by an amount which allows an axial movement of said rod between said projections.

5. The locking tool of claim 2, comprising a rivet joint for fastening said pressure piece to said handle part.

6. The locking tool of claim 2, wherein said second end of said handle part has a portion with a hexagonal outer contour.

7. The locking tool of claim 1, comprising a pressure member for acting upon said head, said pressure member having a diameter which is larger than said predetermined diameter of said rod, said pressure piece engaging said pressure member when screwed into said seat part.

8. The locking tool of claim 7, wherein said pressure member has a cylindrical outer contour sized to allow an axial sliding movement of said pressure member within said second bore.

9. The locking tool of claim 7, wherein said pressure member has a spherical countersink recess formed on a side thereof facing said head of said screw member, said countersink recess having a radius which is substantially equal to a radius of said spherical segment shaped portion of said head.

10. The locking tool of claim 9, wherein said pressure member has a cylinder segment-shaped recess formed on its side opposite to said head, said recess having a cylinder radius which is substantially equal to the radius of said rod.

11. The locking tool of claim 8, wherein said projection has a length dimensioned to leave an axial gap between said pressure piece and said rod in a screwed-in position with said projection acting upon said head or said pressure member, respectively.

12. A locking tool for locking a relative movement between a seat part and a head of a polyaxial bone screw, said locking tool comprising:

a handle part having a central longitudinal axis, a lateral outer surface, a face perpendicular to the longitudinal axis and an external screw thread portion formed in said lateral outer surface adjacent to said face for screwing said handle part into said seat part, a fork-shaped pressure piece, and means for rotatably connecting said pressure piece to said handle part at said face around said central longitudinal axis of said handle part.

* * * * *